United States Patent
Vijayakumari et al.

(10) Patent No.: US 9,505,670 B2
(45) Date of Patent: *Nov. 29, 2016

(54) PROCESS FOR THE PREPARATION OF AN OLEFINIC PRODUCT FROM AN OXYGENATE

(71) Applicant: SHELL OIL COMPANY, Houston, TX (US)

(72) Inventors: Sivakumar Sadasivan Vijayakumari, Gonzales, LA (US); Jeroen Van Westrenen, Amsterdam (NL)

(73) Assignee: Shell Oil Company, Houston, TX (US)

(*) Notice: Subject to any disclaimer, the term of this patent is extended or adjusted under 35 U.S.C. 154(b) by 50 days.

This patent is subject to a terminal disclaimer.

(21) Appl. No.: 14/655,348

(22) PCT Filed: Dec. 24, 2013

(86) PCT No.: PCT/EP2013/078004
§ 371 (c)(1),
(2) Date: Jun. 25, 2015

(87) PCT Pub. No.: WO2014/102290
PCT Pub. Date: Jul. 3, 2014

(65) Prior Publication Data
US 2015/0353441 A1 Dec. 10, 2015

(30) Foreign Application Priority Data
Dec. 28, 2012 (EP) .................... 12199568

(51) Int. Cl.
*C07C 1/20* (2006.01)
*C07C 7/00* (2006.01)

(52) U.S. Cl.
CPC ............. *C07C 1/20* (2013.01); *C07C 7/005* (2013.01); *Y02P 30/42* (2015.11); *Y02P 30/48* (2015.11)

(58) Field of Classification Search
CPC ....................................................... C07C 1/00
USPC ....... 585/638, 639, 640, 641, 802, 809, 820, 585/822, 833
See application file for complete search history.

(56) References Cited

U.S. PATENT DOCUMENTS

| | | | | |
|---|---|---|---|---|
| 6,303,841 | B1* | 10/2001 | Senetar | C07C 11/04 585/638 |
| 6,488,856 | B2* | 12/2002 | Cossee | C10G 31/11 585/648 |
| 8,722,954 | B2* | 5/2014 | Thoret Bauchet | B01D 53/1493 585/809 |
| 2005/0038304 | A1* | 2/2005 | Van Egmond | C07C 1/20 585/324 |
| 2007/0203382 | A1 | 8/2007 | Senetar | |

FOREIGN PATENT DOCUMENTS

| | | |
|---|---|---|
| CN | 101157593 | 4/2008 |
| WO | 2006012150 | 2/2006 |
| WO | 2007111744 | 10/2007 |

\* cited by examiner

*Primary Examiner* — Sharon Pregler

(57) ABSTRACT

The invention relates to a process for the preparation of an olefinic product comprising ethylene and/or propylene from an oxygenate comprising: a) an oxygenate conversion step wherein a gaseous effluent comprising olefins is obtained; b) separation of water from the effluent; c) compression of the effluent; d) acid gas removal from the effluent wherein the water-depleted compressed gaseous effluent is treated with a caustic solution in a caustic tower and a non-aqueous liquid stream comprising one or more aromatic $C_7^+$ hydrocarbons is added to the caustic solution to control the formation of red oil; and e) separating the olefinic product from the gaseous effluent treated in step d).

14 Claims, 1 Drawing Sheet

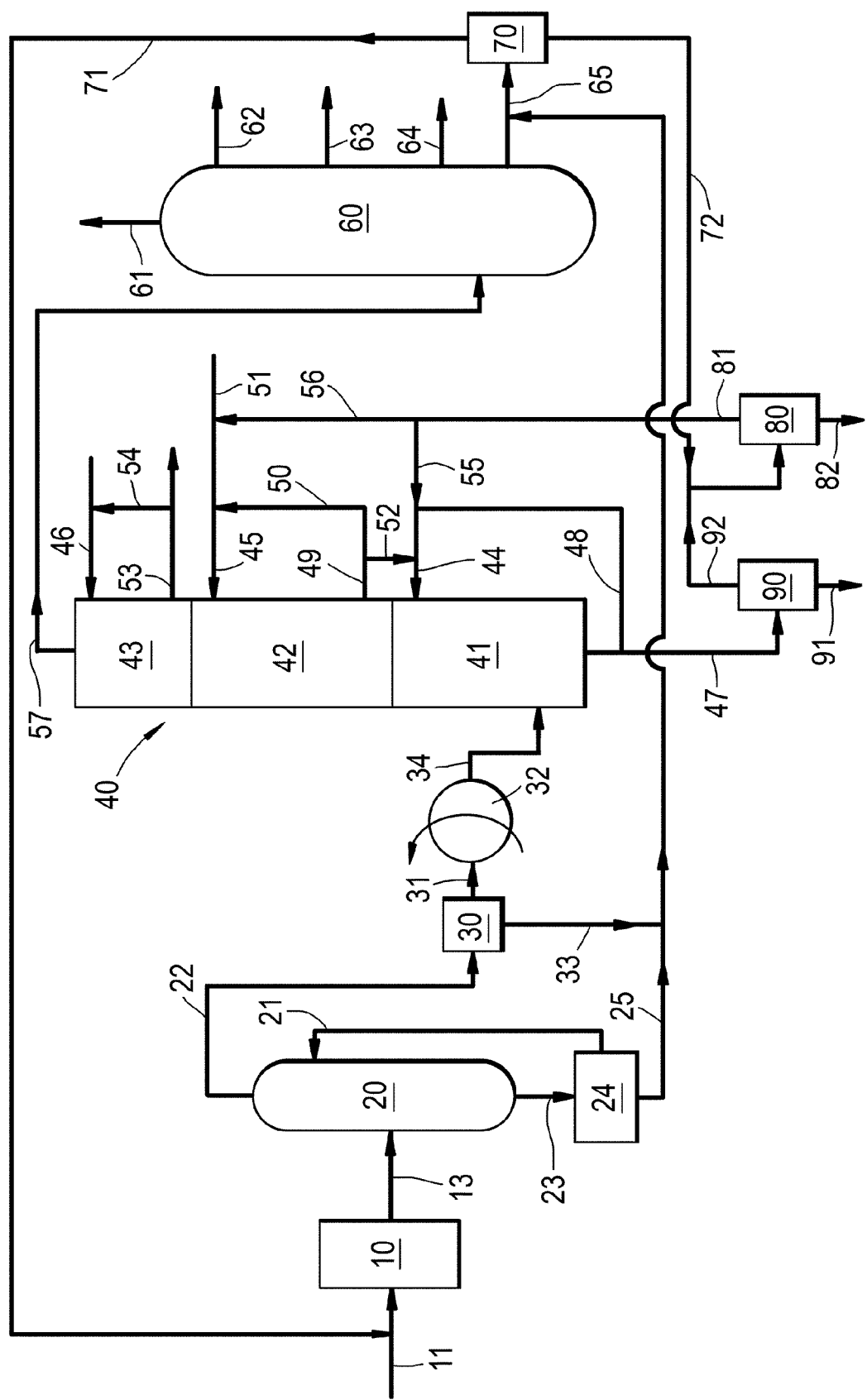

PROCESS FOR THE PREPARATION OF AN OLEFINIC PRODUCT FROM AN OXYGENATE

PRIORITY CLAIM

The present application is the National Stage (§371) of International Application No. PCT/EP2013/078004, filed Dec. 24, 2013, which claims priority from European Patent Application 12199568.2, filed Dec. 28, 2012 incorporated herein by reference.

FIELD OF THE INVENTION

The invention relates to a process for the preparation of an olefinic product comprising ethylene and/or propylene from an oxygenate.

BACKGROUND TO THE INVENTION

Conventionally, ethylene and propylene are produced via steam cracking of paraffinic feedstocks including ethane, propane, naphtha and hydrowax. An alternative route to ethylene and propylene is an oxygenate-to-olefin (OTO) process. Interest in OTO processes for producing ethylene and propylene is growing in view of the increasing availability of natural gas. Methane in the natural gas can be converted into for instance methanol or dimethylether (DME), both of which are suitable feedstocks for an OTO process.

In an OTO process, an oxygenate such as methanol or dimethylether is provided to a reaction zone of a reactor comprising a suitable conversion catalyst and converted into ethylene and propylene. In addition to the desired ethylene and propylene, a substantial part of the oxygenate such as methanol is converted into higher hydrocarbons including $C4^+$ olefins, paraffins and carbonaceous deposits on the catalyst. The effluent from the reactor comprising the olefins, any unreacted oxygenates such as methanol and dimethylether and other reaction products such as water may then be treated to provide separate component streams. Unreacted oxygenates can be separated from the reaction effluent, for instance by contacting with a cooled aqueous stream in a quench tower.

In order to increase the ethylene and propylene yield of the process, the $C4^+$ olefins may be recycled to the reaction zone or alternatively further cracked in a dedicated olefin cracking zone to produce further ethylene and propylene.

Due to the high temperatures in the reaction zone and the acidity of the catalyst, a portion of the oxygenates such as methanol may unavoidably decompose thermally or catalytically into oxides of carbon, i.e. carbon monoxide and carbon dioxide in the gaseous form. The carbonaceous deposits on the catalyst can be removed by the periodic regeneration of the catalyst by heating it with an oxidising gas such as oxygen, in order to burn off the deposits.

Carbon dioxide generated during the OTO process is an acid gas which is thus present in the effluent from the reactor. In order to prevent contamination of the olefinic product and problems associated with the formation of solid carbon dioxide during the separation of the olefinic product into olefinic component streams, which may be carried out at cryogenic temperatures, carbon dioxide should be removed from the reaction effluent and from the gaseous effluent from the quench tower before separation into olefinic component streams. This is typically done by washing the gaseous effluent with a caustic solution in a caustic tower.

Carbonyl compounds, such as aldehydes and ketones, in particular acetaldehyde, are commonly generated by the catalyst in side reactions and are also found in the effluent from the reactor. Carbonyl compounds may build up in the caustic solution used to remove carbon dioxide and other acid gases. The basic components of the caustic solution, such as hydroxide ions, can catalyse the aldol condensation and subsequent dehydration reactions of particularly acetaldehyde to form unsaturated aldehydes such as acrolein, especially at higher pH, such as a pH above 9. Unsaturated aldehydes may polymerise when allowed to accumulate in the caustic solution and if the aldol condensation reaction is left unchecked, a viscous oily polymer can be formed, known as 'red oil', which is insoluble in the caustic solution and can deposit on equipment internals, causing fouling and leading to maloperation of the caustic tower containing the caustic solution.

WO 2007/111744 discloses a process for oxygenate conversion to olefins with enhanced carbonyl recovery. A recycle or circulated water stream is treated with a sulphite-containing material in order to form a treated water stream with an appropriately reduced or minimised carbonyl, in particular aldehyde, content. The sulphite-containing material is added to the oxygenate absorber zone. The oxygenate-rich water stream containing unreacted sulphite and bisulphite addition compounds produced in the oxygenate absorber zone is passed to an oxygenate stripper zone to be separated into an oxygenate-containing stream and a recycle water stream. The oxygenate-containing stream can be returned to the oxygenate conversion reactor. The recycle water stream can be passed to a wash water stripper to recover oxygenates and provide a bottoms water stream comprising unreacted sulphite and bisulphite addition compounds which can be passed to the effluent treatment zone for the treatment of the reactor section effluent. The recycle water stream can also be passed to the oxygenate absorber zone for the treatment of the compressed oxygenate conversion effluent stream.

A disadvantage of the process of WO2007/11174 is, however, that a stream comprising unreacted sulphite and bisulphate addition compounds is treated in the effluent treatment system of the OTO process. This may result in undesired release of acetaldehyde from its addition compound, since the formation of formaldehyde addition products is favoured. Moreover, a sulphur-containing waste stream will be formed in an olefins-to-oxygenate process that normally produces a sulphur-free effluent.

SUMMARY OF THE INVENTION

It has now been found that deposition on equipment internals of so-called red oil formed in the caustic treatment of an olefinic effluent stream of an oxygenate-to-olefins process can be avoided or at least minimised without applying a treatment step with bi-sulphite. By mixing a non-aqueous liquid stream comprising one or more aromatic $C7^+$ hydrocarbons with the alkaline solution(s) used to wash the olefinic effluent stream in the caustic treatment, the amount of red oil in the caustic tower can be adequately controlled and undesired fouling of equipment internals can be avoided. Any aldol condensation products and any subsequent dehydration and/or polymerisation products thereof formed during the caustic treatment dissolve in the liquid aromatic hydrocarbon stream that is mixed with the alkaline solution used to wash the olefinic stream and are discharged from the caustic tower with the spent caustic solution.

Accordingly, the present invention provides a process for the preparation of an olefinic product comprising ethylene and/or propylene from an oxygenate, the process comprising the following steps:

a) contacting the oxygenate in an oxygenate conversion reaction zone with a molecular sieve-comprising catalyst at a temperature in the range of from 350 to 1000° C. to produce an oxygenate conversion effluent comprising olefins, water, carbon dioxide and carbonyl compounds including $C2^+$ aldehyde and/or ketone;

b) separating water from the oxygenate conversion effluent to obtain a water-depleted gaseous oxygenate conversion effluent comprising olefins, carbon dioxide and $C2^+$ aldehyde and/or ketone;

c) compressing the water-depleted gaseous effluent with the optional removal of any condensed phase to obtain a compressed gaseous stream comprising olefins, carbon dioxide and $C2^+$ aldehyde and/or ketone;

d) separating carbon dioxide from the compressed gaseous stream by subjecting the compressed gaseous stream to a caustic wash treatment in a caustic tower wherein the gaseous stream is countercurrently contacted with a caustic solution to obtain a washed gaseous stream comprising olefins; and e) subjecting the washed gaseous stream to one or more separation steps such that at least an olefin product stream comprising ethylene and/or propylene is obtained, wherein in step d) a non-aqueous liquid stream comprising one or more aromatic $C7^+$ hydrocarbons is added to the caustic solution prior to contacting the caustic solution with the gaseous stream and wherein a liquid phase comprising spent caustic solution and the one or more aromatic $C7^+$ hydrocarbons is discharged from the caustic tower.

An important advantage of the process according to the invention is that removal of carbonyl compounds like acetaldehyde prior to the caustic treatment is not needed. Moreover, the liquid aromatic hydrocarbon stream used for removal of red oil and precursors thereof may advantageously be a stream recovered from the process according to the invention, in particular a $C7^+$ hydrocarbon stream that is in separation step e) recovered from the washed gaseous stream obtained in caustic treatment step d).

BRIEF DESCRIPTION OF THE DRAWING

The FIGURE schematically shows a line-up of the process according to the invention.

DETAILED DESCRIPTION OF THE INVENTION

In the process according to the invention, an olefinic product comprising ethylene and/or propylene is prepared by first converting the oxygenate into olefins in a so-called oxygenate conversion step (step a)) to produce an effluent comprising olefins, water, carbon dioxide and carbonyl compounds including $C2^+$ aldehyde and/or ketone. In step b), water is separated from the oxygenate conversion effluent to obtain a water-depleted gaseous oxygenate conversion effluent comprising olefins, carbon dioxide and $C2^+$ aldehyde and/or ketone. In subsequent step c), the water-depleted gaseous effluent obtained in step b) is compressed to obtain a compressed gaseous stream comprising olefins, carbon dioxide and $C2^+$ aldehyde and/or ketone. In step d), carbon dioxide and other acids are separated from the compressed gaseous stream by subjecting the compressed gaseous stream to a caustic wash treatment, wherein the gaseous stream is countercurrently contacted with a caustic solution. In order to minimise deposition of polymerised condensation products of aldehydes and/or ketones on equipment internals, a non-aqueous liquid stream comprising one or more aromatic $C7^+$ hydrocarbons is added to the caustic solution in step d). In step d), a washed gaseous stream comprising olefins is obtained. This stream is subjected in step e) to one or more separation steps to obtain at least an olefin product stream comprising ethylene and/or propylene.

In a first step, an oxygenate is converted into lower olefins, i.e. ethylene and propylene, by contacting the oxygenate with a molecular sieve-comprising catalyst at a temperature in the range of from 350 to 1000° C. (oxygenate conversion step a)).

Reference herein to an oxygenate is to a compound comprising at least one alkyl group that is covalently linked to an oxygen atom. Preferably, the at least one alkyl group has up to five carbon atoms, more preferably up to four, even more preferably one or two carbon atoms, most preferably is methyl. Mono-alcohols and dialkylethers are particularly suitable oxygenates. Methanol, dimethylether and mixtures thereof are examples of particularly preferred oxygenates. Most preferably, the oxygenate is methanol.

Oxygenate conversion step a) is carried out by contacting the oxygenate with a molecular sieve-comprising catalyst at a temperature in the range of from 350 to 1000° C., preferably of from 350 to 750° C., more preferably of from 450 to 700° C., even more preferably of from 500 to 650° C. The conversion may be carried out at any suitable pressure, preferably at a pressure in the range of from 1 bar to 50 bar (absolute), more preferably of from 1 bar to 15 bar (absolute). A pressure in the range of from 1.5 to 4.0 bar (absolute) is particularly preferred.

Any molecular sieve comprising catalyst known to be suitable for the conversion of oxygenates, in particular alkanols and dialkylethers, into lower olefins may be used. Preferably the catalyst comprises a molecular sieve having a 8-, 10- or 12-ring structure and an average pore size in the range of from 3 ↑ to 15 Å. Examples of suitable molecular sieves are silicoaluminophosphates (SAPOs), aluminophosphates (ALPO), metal-substituted aluminophosphates or metal-substituted silicoaluminophosphates. Preferred SAPOs include SAPO-5, -8, -11, -17, -18, -20, -31, -34, -35, -36, -37, -40, -41, -42, -44, -47 and -56. SAPO-17, -18, -34, -35, and -44 are particularly preferred.

A particular suitable class of molecular sieves are zeolites, more in particular a zeolite with a 10-membered ring structure. Zeolite-comprising catalysts are known for their ability to convert higher olefins into lower olefins, in particular to convert $C4^+$ olefins into ethylene and/or propylene. Suitable zeolite-comprising catalysts include those containing a zeolite of the ZSM group, in particular of the MFI type, such as ZSM-5, the MTT type, such as ZSM-23, the TON type, such as ZSM-22, the MEL type, such as ZSM-11, the FER type. Other suitable zeolites are for example zeolites of the STF-type, such as SSZ-35, the SFF type, such as SSZ-44 and the EU-2 type, such as ZSM-48. Preferably, the catalyst comprises at least one zeolite selected from MFI, MEL, TON and MTT type zeolites, more preferably at least one of ZSM-5, ZSM-11, ZSM-22 and ZSM-23 zeolites.

The zeolite in the oxygenate conversion catalyst is preferably predominantly in the hydrogen form. Preferably at least 50 wt %, more preferably at least 90 wt %, even more preferably at least 95 wt %, still more preferably at least 100 wt % of the zeolite is in the hydrogen form.

The molecular sieve-comprising catalyst may further comprise a binder material such as for example silica, alumina, silica-alumina, titania, or zirconia, a matrix material such as for example a clay, and/or a filler. Besides lower olefins, $C4^+$ hydrocarbons including $C4^+$ paraffins, $C4^+$ olefin, and aromatic hydrocarbons like benzene, toluene and C8 aromatics, such as xylenes and ethylbenzene, are formed as by-product. Thus, an oxygenate conversion effluent comprising ethylene, propylene and $C4^+$ hydrocarbons is produced in step a).

In oxygenate conversion step a), not only lower olefins and $C4^+$ hydrocarbons, but also water is formed. In step b), water is separated from the gaseous oxygenate conversion effluent. Such separation step is well-known in the art and typically comprises passing the effluent to a separation zone, such as a gas/liquid contactor, preferably a column comprising packing and/or trays also known as quench water tower, wherein the gaseous effluent is contacted with an aqueous stream, typically water. The aqueous stream can condense water from the gaseous effluent and also some higher hydrocarbons, typically $C7^+$ hydrocarbons, and can absorb any unreacted oxygenate to obtain a water-depleted gaseous oxygenate conversion effluent comprising olefins, carbon dioxide and $C2^+$ aldehyde and/or ketone and an aqueous stream comprising water, condensed hydrocarbons and typically also unconverted oxygenate. The aqueous stream is typically recycled over the quench water tower, preferably after removal of any condensed hydrocarbon, for example in a quench water settler. The removed condensed hydrocarbons typically are C7+ hydrocarbons and can advantageously be used as part of the non-aqueous liquid stream comprising one or more aromatic $C7^+$ hydrocarbons that is added to the caustic solution in step d).

In step c), the water-depleted gaseous effluent obtained in step b) is compressed. This may be done in any suitable compressor. The compressor may be a single stage or a multi-stage compressor. Preferably, a multi-stage centrifugal compressor is used. The water-depleted gaseous effluent is preferably compressed to a pressure of at least 5 bar (absolute), more preferably at least 9 bar (absolute). Preferably, the water-depleted gaseous effluent is compressed to a pressure of at most 45 bar, more preferably at most 20 bar (absolute). Any condensed phase such as water and condensed $C5^+$ hydrocarbons may be removed from the compressed stream, for example by means of one or more gas-liquid separators, such as for example knock-out drums. In a multi-stage compression step, condensed phase may be removed after each compression stage. The removed condensed hydrocarbons may be used as part of the non-aqueous liquid stream comprising one or more aromatic $C7^+$ hydrocarbons that is added to the caustic solution in step d).

In the process according to the invention, the gaseous stream comprising olefins may be further compressed after caustic wash treatment step d). It will be appreciated that the pressure to which the stream is compressed in step c), i.e. prior to the caustic treatment, will inter alia depend on whether there is a further compression step provided for the washed gaseous stream, i.e. between caustic treatment step d) and separation step e).

In step c) is thus obtained a compressed gaseous stream comprising olefins, carbon dioxide and $C2^+$ aldehyde and/or ketone.

In step d), the compressed gaseous stream is subjected to a caustic wash treatment in a caustic tower in order to separate carbon dioxide from the compressed gaseous stream. Caustic wash treatments for removal of acid gases are well known in the art. In such treatment, the gaseous stream to be treated is countercurrently contacted with a caustic solution, and optionally in a final stage with a water stream, to obtain a washed gaseous stream.

Any known process conditions and tower configurations for caustic treatments for acid gas removal may suitably be used in the process according to the invention. Preferably, the gaseous stream is countercurrently contacted with a caustic solution in at least two stages in series, more preferably in two or three stages, most preferably in two stages. In case of at least two stages, the gaseous stream is contacted in each stage with a caustic solution having a concentration of caustic, wherein the concentration of caustic in a next stage is higher than the concentration of caustic in the stage directly preceding said next stage. Thus, the concentration of the caustic solution in the second stage is higher than the concentration of the caustic solution in the first stage. Reference herein to the first stage is to the first stage with regard to the direction of flow of the gaseous stream to be treated. Thus, the first stage is the lowest stage, i.e. the stage wherein the gaseous stream is entering the caustic tower.

The caustic solution is an aqueous alkaline stream suitable to absorb acid gases. Such caustic solutions are known in the art. Any suitable caustic solution may be used, preferably a solution of an alkali metal hydroxide such a sodium hydroxide or potassium hydroxide. The caustic solution may have any suitable concentration of caustic, preferably in the range of from 0.5 to 2.5 moles of hydroxide ions per liter (equivalent to 2 to 10 wt % sodium hydroxide based on the weight of water).

In case of two caustic stages, the concentration of the caustic solution in the first stage is preferably in the range of from 0.5 to 1.0 moles of hydroxide ions per liter (equivalent to 2 to 4 wt % sodium hydroxide); in the second stage in the range of from 1.25 to 2.5 moles of hydroxide ions per liter (equivalent to 5 to 10 wt % sodium hydroxide).

In the caustic tower, the gaseous stream is countercurrently contacted with a caustic solution in one or more stages, usually two or three stages. Preferably, the gaseous stream is countercurrently washed with a water stream in a final stage. Typically, each caustic stage and, if present, the water stage is carried out in a separate section of the tower. In each section, liquid extractant (caustic solution or water stream) is supplied to the top of the section and discharged from the bottom of the section. The gaseous stream is supplied to the bottom of each section and withdrawn via the top to the next section or a work-up section. Fresh caustic solution is typically supplied to the most concentrated solution, i.e. to the last caustic section. Caustic solution withdrawn from the bottom of a section is partially recycled to the top of that section and partially supplied to the top of the preceding section as make-up of the losses of caustic (e.g. sodium hydroxide) as a result of the reaction of the caustic with carbon dioxide and other acids. Caustic solution withdrawn from the bottom of the first section is partially recycled to the top of the first section and partially withdrawn from the caustic tower as spent caustic.

The operating temperature in the caustic tower may be any suitable temperature. Preferably, the operating temperature is at most 50° C., more preferably in the range of from 35 to 45° C. The pressure may be any pressure known to be suitable for a caustic wash treatment, preferably in the range of from 9 to 45 bar, more preferably of from 10 to 20 bar (absolute).

Preferably, the compressed gaseous stream to be treated in step d) is superheated before entering the caustic tower in order to avoid undesired condensation of hydrocarbons in the caustic tower. More preferably, the compressed gaseous stream obtained in step c) is heated to a temperature in the range of from 2 to 5° C. above its dew point prior to subjecting the compressed gaseous stream to the caustic wash treatment in step d). Preferably, the temperature of the compressed gaseous stream that is contacted with the caustic solution is at most 40° C.

In the process according to the invention, a non-aqueous liquid stream comprising one or more aromatic $C7^+$ hydrocarbons is added to the caustic solution prior to contacting the caustic solution with the gaseous stream and a liquid phase comprising spent caustic solution, the one or more aromatic hydrocarbons, including any polymer dissolved therein, is discharged from the caustic tower.

In the preferred embodiment wherein the compressed gaseous stream is countercurrently contacted with a caustic solution in at least two stages in series before being countercurrently contacted with the water stream, the non-aqueous liquid stream is added to the caustic solution of at least one stage and liquid phase comprising spent caustic solution and the one or more aromatic hydrocarbons is discharged from the first stage. More preferably, the non-aqueous liquid stream is at least added to the caustic solution that is supplied to the first stage, i.e. at least to the caustic solution that is supplied to the top of the first section. In a particularly preferred embodiment, the non-aqueous liquid stream is added to the caustic solution in all of the at least two stages, i.e. in each stage the non-aqueous liquid stream is added to the caustic solution supplied to the top of the section wherein that stage is carried out.

If a final water wash stage is present, the non-aqueous liquid stream may also be added to the water stream prior to countercurrently contacting the water stream with the gaseous stream.

The non-aqueous liquid stream comprising one or more $C7^+$ aromatic hydrocarbons may be any liquid hydrocarbon stream that is able to serve as a solvent for polymerisation products of condensed aldehydes/ketones (so-called red oil) that are typically formed under the conditions applied in caustic towers for acid gas removal.

Preferably, the non-aqueous liquid stream essentially consists of $C7^+$ hydrocarbons, more preferably essentially consists of $C8^+$ hydrocarbons. In order to be able to sufficiently dissolve the polymerisation products formed, the non-aqueous liquid stream comprises one or more aromatic hydrocarbons, more preferably $C7^+$ aromatic hydrocarbons, even more preferably $C8^+$ aromatic hydrocarbons. A non-aqueous liquid stream comprising C8 aromatic hydrocarbons such as xylene and/or ethylbenzene is particularly preferred. Preferably, the non-aqueous liquid stream comprises at least 30 vol % aromatic $C7^+$ hydrocarbons, more preferably at least 50 vol.

Reference herein to a stream essentially consisting of certain hydrocarbons is to a stream that comprises at least 90 vol %, preferably at least 95 vol % of such hydrocarbons.

In order to minimise the formation of polymerisation products, the non-aqueous liquid stream preferably comprises no or a minimum amount of olefinic hydrocarbons. Preferably, the non-aqueous liquid stream comprises less than 0.1 wt %, more preferably less than 0.05 wt % of olefinic hydrocarbons.

A suitable non-aqueous liquid stream is hydrotreated pyrolysis gasoline.

More preferably, the non-aqueous liquid stream is a stream, or comprises part of a stream, that is recovered from the oxygenate conversion effluent in step b), step c), and/or step e), i.e. hydrocarbons that are condensed in water-separation step b), hydrocarbons that are condensed in compression step c), and/or a stream comprising $C7^+$ hydrocarbons that is obtained in separation step e). Condensed hydrocarbons obtained in step b) or in step c) may be combined with a stream obtained in separation step e) to undergo a further combined separation step before being added to the caustic solution in step d).

Even more preferably, the non-aqueous liquid stream is a stream, or comprises part of a stream, comprising $C7^+$ hydrocarbons that is separated in step e) from the washed gaseous stream, optionally after combination of condensed hydrocarbons recovered in step b) and/or step c) with a $C5^+$ stream obtained in one of the separation steps within step e). In a particularly preferred embodiment of the invention, an aromatic stream comprising C8 aromatic hydrocarbons, i.e. xylene and optionally ethylbenzene, separated in step e) from the washed gaseous stream is used as the non-aqueous liquid stream.

The non-aqueous stream comprising aromatic hydrocarbons serves to minimise the residence time of any aldol condensation products formed and therewith limit the growth of the polymer chain of any polymerisation products from such aldol condensation products. It will be appreciated that the amount of non-aqueous stream needed to serve this purpose will depend on the composition of the compressed gaseous stream, in particular the concentration of aldehydes and ketones in the compressed gaseous stream, and of the process condition in the caustic wash treatment.

Preferably, the amount of non-aqueous liquid stream added to the caustic solution is such that in the liquid phase comprising spent caustic solution and the one or more aromatic $C7^+$ hydrocarbons, the mass ratio of non-aqueous phase and aqueous phase is in the range of from 0.1 to 1.0, more preferably of from 0.2 to 0.8, even more preferably of from 0.3 to 0.5.

The non-aqueous liquid stream comprising one or more aromatic hydrocarbons may be continuously or batch-wise added to the caustic solution.

In separation or work-up step e), the washed gaseous stream comprising olefins obtained in step d) is subjected to one or more separation steps to obtain at least an olefin product stream comprising ethylene and/or propylene. In this step, the washed gaseous stream is typically first dried and then separated into different fractions by means known in the art. Preferably, a fraction comprising mainly ethylene is first separated from the washed gaseous stream in a de-ethaniser and a fraction mainly comprising propylene is separated from the bottoms of the de-ethaniser in a de-propaniser. The bottoms of the de-propaniser contain $C4^+$ hydrocarbons. Alternatively, a fraction comprising both ethylene and propylene may be separated from the washed gaseous stream to obtain an olefinic product stream comprising both ethylene and propylene.

The $C4^+$ hydrocarbon fraction obtained as bottoms of a de-propaniser is preferably further separated into a fraction comprising $C5^+$ hydrocarbons and a fraction comprising C4 hydrocarbons, mainly C4 olefins, in for example a de-butaniser. The fraction comprising C4 hydrocarbons may be recycled to step a) to convert C4 olefins into additional ethylene and propylene.

In the process according to the invention, a stream comprising $C7^+$ hydrocarbons, preferably a stream comprising $C8^+$ hydrocarbons, more preferably a stream comprising C8-C10 hydrocarbons is separated from the washed gaseous stream. This may suitably be done by first separating a fraction comprising $C5^+$ hydrocarbons as described hereinabove and then further fractionating by means known in the art the C5+ hydrocarbon fraction to obtain a C5-C7 hydrocarbon fraction and a C8+ hydrocarbon fraction, or even further fractionating the C8+ fraction to obtain a C8-C10 hydrocarbon fraction and a C10+ hydrocarbon fraction.

Preferably, a stream with a relatively high content in C8 aromatic hydrocarbons is obtained in step e) by separating the C5+ hydrocarbon fraction into a C5-C7 hydrocarbon fraction and a C8+ hydrocarbon fraction that might be further separated into a C8-C10 hydrocarbon fraction and a C10+ hydrocarbon fraction. The C5-C7 hydrocarbon fraction comprises C5-C7 hydrocarbons including aromatic hydrocarbons such as benzene and toluene. The C8+ or C8-C10 hydrocarbon fraction includes C8 aromatic hydrocarbons such as xylenes and optionally ethylbenzene. More preferably, the C5-C7 hydrocarbon fraction is recycled to oxygenate conversion step a) wherein benzene and/or toluene might be alkylated to form xylene. As a result the content of aromatic hydrocarbons, in particular xylene, in the C8+ or C8-C10 hydrocarbon fraction will increase.

Preferably, the C7+ hydrocarbon fraction, more preferably the C8+ fraction, even more preferably the C8-C10 hydrocarbon fraction obtained in step e) is used as the non-aqueous liquid stream comprising one or more aromatic C7+ hydrocarbons. Preferably, the fraction used as the non-aqueous liquid stream is treated to decrease the content of olefinic hydrocarbons, in particular di-olefinic hydrocarbons, prior to being supplied to step d). This may for example be done by means of hydrotreating or by means of a clay treatment.

At the bottom of the first section of the caustic tower, a liquid phase comprising spent caustic solution and the one or more aromatic C7+ hydrocarbons that were added with the non-aqueous stream and any polymer dissolved in the aromatic hydrocarbons is present. Part of this liquid phase is recycled to the top of the first section and part of this liquid phase is discharged from the tower. Preferably, the liquid phase that is discharged is separated into an aqueous phase comprising spent caustic solution and a non-aqueous phase comprising the one or more aromatic hydrocarbons and dissolved polymer. Such separation may be done by any means known in the art for separating an aqueous and a non-aqueous phase, for example by means of a decanter.

The non-aqueous phase comprising the one or more aromatic hydrocarbons and dissolved polymer may be withdrawn from the process. Preferably, dissolved polymer is separated from the one or more aromatic hydrocarbons, for example by means of distillation, and the one or more aromatic hydrocarbons are recycled to step d) as (part of) the non-aqueous liquid stream that is added to the caustic solution.

In a preferred embodiment of the invention, the non-aqueous phase comprising the one or more aromatic C7+ hydrocarbons and dissolved polymer is supplied to a fractionator used in step e) of the process, i.e. the work-up section for the washed gaseous stream, that separates C10+ hydrocarbons or higher hydrocarbons from lower hydrocarbons. The dissolved polymers will then be removed from the process with the C10+ or higher hydrocarbon fraction. The lower hydrocarbons, e.g. a fraction from the washed gaseous stream comprising C7-C10 or preferably C8-C10 hydrocarbons and the C10+ hydrocarbons from the non-aqueous phase separated from liquid phase from the caustic tower, are then suitably used as the non-aqueous liquid stream added to the caustic solution in step d), preferably after a treatment to remove diolefins.

In a preferred embodiment, the colour of the liquid phase discharged from the caustic tower is determined or the colour of the non-aqueous phase separated from the liquid phase discharged from the caustic tower is determined. The amount of non-aqueous liquid stream added to the caustic solution is controlled in accordance with the determined colour.

Colour determination may be carried out by any suitable means in the art. Colour determination may for example be done by visual inspection, preferably through sight glasses in a withdrawal and/or recycle conduit for the liquid phase or the non-aqueous phase separated from such liquid phase. Alternatively, colour determination may be done by automated colour measurements, for example IR or UV-VIS measurements. Such automated measurements may be carried out in situ or ex situ on samples taken from the liquid phase or the non-aqueous phase separated from such liquid phase.

DETAILED DESCRIPTION OF THE DRAWING

In the FIGURE is schematically shown a line-up of the process according to the invention. Methanol is supplied to oxygenate conversion reaction zone 10 via line 11 and converted into an oxygenate conversion effluent comprising olefins, water, carbon dioxide and acetaldehyde. The effluent is supplied via conduit 13 to quench water tower 20 wherein it is contacted with water that is supplied via conduit 21, to provide a water-depleted gaseous olefinic stream that is discharged from tower 20 via conduit 22. A liquid phase comprising water and some condensed hydrocarbons is discharged via conduit 23 and separated in settler 24 in a water phase that is recycled to tower 20 via conduit 21 and a hydrocarbon phase that is discharged via conduit 25.

The water-depleted gaseous olefinic stream is supplied via conduit 22 to compression zone 30 to provide a compressed gaseous stream. The compressed gaseous stream is supplied via conduit 31 to superheater 32. Any condensed hydrocarbons are removed from compression zone 30 via conduit 33. Superheated compressed gaseous stream obtained in superheater 32 is supplied via conduit 34 to caustic tower 40 to be countercurrently extracted with sodium hydroxide. Caustic tower 40 has two sections 41, 42 for caustic treatment and water wash section 43. The superheated compressed gaseous stream is supplied via conduit 34 to the lower part of first section 41 and countercurrently contacted in section 41 with 2 wt % sodium hydroxide that is supplied to the top of section 41 via conduit 44. In second section 42, the gaseous stream is countercurrently contacted with 10 wt % sodium hydroxide that is supplied to the top of section 42 via conduit 45. In final section 43, the gaseous stream is contacted with a water stream supplied via conduit 46.

Liquid phase is withdrawn from the bottom of section 41 via conduit 47 and partially recycled to section 41 via conduit 48. Used caustic is withdrawn from section 42 via conduit 49 and partly recycled to section 42 via conduit 50 to form, together with fresh caustic solution supplied via conduit 51, the caustic solution supplied to section 42. Part of the used caustic withdrawn from section 42 is supplied to preceding section 41 via line 52. Spent water is withdrawn from the bottom of section 43 via conduit 53 and partly recycled to the top of section 43 via line 54 and partly withdrawn from the process. A hydrocarbon stream comprising xylene is added via lines 55 and 56, respectively, to the used caustic recycled to section 41 and to the fresh caustic supplied to section 42. Additionally, the hydrocarbon stream may be added to the water supplied to section 43 (not shown).

Washed gaseous stream is withdrawn from caustic tower 40 via conduit 57 and supplied to work-up section 60. In work-up section 60, the washed gaseous stream is separated into a light gas stream, an ethylene stream, a propylene stream, a C4 hydrocarbon fraction and a C5$^+$ hydrocarbon fraction, which are withdrawn from section 60 via lines 61, 62, 63, 64 and 65, respectively. Part of the C4 hydrocarbon fraction may be recycled to oxygenate conversion zone 10 for conversion of any olefins therein into lower olefins (not shown).

The C5$^+$ hydrocarbon fraction in line 65 is combined with the hydrocarbon phase from settler 24 of the quench water tower and hydrocarbon phase from compression section 30. In further fractionator 70, the combined C5$^+$ hydrocarbon fraction and hydrocarbon phases from the quench water tower and the compression section are separated into a C5-C7 hydrocarbon fraction comprising benzene and toluene and a C8$^+$ hydrocarbon fraction comprising xylene. The fraction comprising benzene and toluene is recycled via conduit 71 to oxygenate conversion zone 10 to be converted into xylene. The C8$^+$ hydrocarbon fraction is supplied via conduit 72 to fractionator 80 wherein it is separated into a C8-C10 fraction comprising xylene and some ethylbenzene and a C10$^+$ hydrocarbon fraction. The C8-C10 fraction is hydrotreated to remove any di-olefins (not shown) and at least part of the hydrotreated C8-C10 fraction is added to the caustic solutions to be supplied to sections 41 and 42 of caustic tower 40 via conduit 81. The liquid phase that is discharged from tower 40 via conduit 47 comprises spent caustic solution, hydrocarbons added to tower 40 with the C8-C10 hydrocarbon fraction, and any polymer dissolved therein. In decanter 90, the liquid phase is separated into an aqueous phase comprising spent caustic solution that is withdrawn via conduit 91 and into a non-aqueous phase comprising C8-C10 hydrocarbons and dissolved polymer. The non-aqueous phase is supplied to fractionator 80 via conduit 92. Any dissolved polymer will end up in the C10$^+$ hydrocarbon fraction that is removed from the process via conduit 82.

The colour of the non-aqueous phase in conduit 92 is determined by visual inspection through a sight glass (not shown) in conduit 92. The amount of C8-C10 hydrocarbon fraction added to the caustic solutions via conduit 81 is adapted in accordance with the colour of the non-aqueous phase in conduit 92. In case the non-aqueous phase would appear to have a light colour and thus a low polymer content, there is no need to send the entire non-aqueous phase to fractionator 80. Part or even all of the non-aqueous phase may then be directly added to the caustic solutions by mixing such part with the C8-C10 hydrocarbon fraction in conduit 81.

That which is claimed is:

1. A process for the preparation of an olefinic product comprising ethylene and/or propylene from an oxygenate, the process comprising the following steps:
    a) contacting the oxygenate in an oxygenate conversion reaction zone with a molecular sieve-comprising catalyst at a temperature in the range of from 350 to 1000° C. to produce an oxygenate conversion effluent comprising olefins, water, carbon dioxide and carbonyl compounds including C2$^+$ aldehyde and/or ketone;
    b) separating water from the oxygenate conversion effluent to obtain a water-depleted gaseous oxygenate conversion effluent comprising olefins, carbon dioxide and C2$^+$ aldehyde and/or ketone;
    c) compressing the water-depleted gaseous effluent with the optional removal of any condensed phase to obtain a compressed gaseous stream comprising olefins, carbon dioxide and C2$^+$ aldehyde and/or ketone;
    d) separating carbon dioxide from the compressed gaseous stream by subjecting the compressed gaseous stream to a caustic wash treatment in a caustic tower wherein the gaseous stream is countercurrently contacted with a caustic solution to obtain a washed gaseous stream comprising olefins; and
    e) subjecting the washed gaseous stream to one or more separation steps such that at least an olefin product stream comprising ethylene and/or propylene is obtained,
    wherein in step d) a non-aqueous liquid stream comprising one or more aromatic C7$^+$ hydrocarbons is added to the caustic solution prior to contacting the caustic solution with the gaseous stream and wherein a liquid phase comprising spent caustic solution and the one or more aromatic C7$^+$ hydrocarbons is discharged from the caustic tower and wherein the non-aqueous liquid stream comprises less than 0.1 wt % of olefinic hydrocarbons and at least part of the non-aqueous liquid stream comprising one or more aromatic C7$^+$ hydrocarbons is recovered from the oxygenate conversion effluent in step b), step c), and/or step e).

2. A process according to claim 1, wherein in step d) the compressed gaseous stream is countercurrently contacted with a caustic solution in at least two stages in series before being countercurrently contacted with the water stream, wherein the gaseous stream is contacted in each stage of the at least two stages with a caustic solution having a concentration of caustic, wherein the concentration of caustic in a next stage is higher than the concentration of caustic in the stage directly preceding said next stage, wherein the non-aqueous liquid stream is added to the caustic solution of at least one stage and wherein the liquid phase comprising spent caustic solution and the one or more aromatic hydrocarbons is discharged from the first stage.

3. A process according to claim 2, where the non-aqueous liquid stream is added to the caustic solution in the first stage.

4. A process according to claim 3, wherein the non-aqueous liquid stream is added to the caustic solution in all of the at least two stages.

5. A process according to claim 1, wherein the non-aqueous liquid stream consists essentially of C7-C10 hydrocarbons.

6. A process according to claim 5, wherein the non-aqueous liquid stream essentially consists of C8-C10 hydrocarbons.

7. A process according to claim 1, wherein the non-aqueous liquid stream comprises xylene.

8. A process according to claim 1, wherein in step e) a stream comprising C7$^+$ hydrocarbons is obtained and wherein the non-aqueous liquid stream comprises at least part of the stream comprising C7$^+$ hydrocarbons.

9. A process according to claim 8, wherein in step e) a stream comprising C8-C10 hydrocarbons is obtained, and wherein the non-aqueous liquid stream comprises at least part of the stream comprising C8-C10 hydrocarbons.

10. A process according to claim 1, wherein the temperature of the compressed gaseous stream that is contacted with the caustic solution is at most 40° C.

11. A process according to claim 1, wherein the caustic wash treatment is operated at a temperature of at most 50° C.

12. A process according to claim 1, wherein the colour of the liquid phase discharged from the caustic tower or of a non-aqueous phase separated from the liquid phase is determined, and wherein the amount of non-aqueous liquid stream added to the caustic solution is controlled in accordance with the determined colour.

13. A process according to claim 12, wherein the colour is determined by inspection through a sight glass located in a conduit for recycling or withdrawal of the liquid phase and/or a conduit for withdrawal of a non-aqueous phase separated from the liquid phase.

14. A process according to claim 1, wherein the compressed gaseous stream obtained in step c) is heated to a temperature in the range of from 2 to 5° C. above its dew point prior to subjecting the compressed gaseous stream to the caustic wash treatment in step d).

\* \* \* \* \*